United States Patent [19]
Logemann et al.

[11] Patent Number: 5,804,184
[45] Date of Patent: Sep. 8, 1998

[54] TRANSGENIC PATHOGEN-RESISTANT ORGANISM

[75] Inventors: Jürgen Logemann, NB Leiden, Netherlands; Guido Jach; Birgit Görnhardt, both of Köln, Germany; John Mundy, V Copenhagen, Denmark; Jeff Schell, Köln, Germany; Peter Eckes, Kelkheim, Germany

[73] Assignee: Max Planck Gesellschaft Zur Furderung der Wissen Schaften, e.v., Gottingen, Germany

[21] Appl. No.: 812,025

[22] Filed: Mar. 6, 1997

Related U.S. Application Data

[62] Division of Ser. No. 457,797, Jun. 1, 1995, Pat. No. 5,689,045, which is a continuation of Ser. No. 134,416, Oct. 8, 1993, abandoned.

[30] Foreign Application Priority Data

Oct. 9, 1992 [DE] Germany ..................... 42 34 131.0

[51] Int. Cl.$^6$ ................. A61K 38/54; A61K 38/47; A61K 38/16
[52] U.S. Cl. ............... 424/94.61; 424/94.2; 514/12; 435/200; 435/209
[58] Field of Search ............... 424/94.2, 94.61; 514/12; 435/200, 209

[56] References Cited

U.S. PATENT DOCUMENTS 4,940,840  7/1990  Suslow et al. ..................... 800/205

FOREIGN PATENT DOCUMENTS 440 304  8/1991  European Pat. Off. .

OTHER PUBLICATIONS

R. Leah et al., "Biochemical and Molecular Characterization of Three Barley Seed Proteins With Antifungal Properties", J. Biol. Chem. 266(3): 1564–1573, Jan. 1991.

S. Wnendt et al., "Cloning and Nucleotide Sequences of a cDNA Encoding the Antifungal–Protein of *Aspergillus giganteus* and Preliminary Characterization of the Native Gene", Nuc. Acid Res. 18(13): 3987, Jul. 1990.

*Primary Examiner*—Rebecca E. Prouty
*Attorney, Agent, or Firm*—Baker & Botts, New York

[57] ABSTRACT

Transgenic pathogen-resistant organism whose genome contains at least two different genes under the control of active promoters with pathogen-inhibiting action. This organism is distinguished by a synergistic pathogen-inhibiting action. This action is evident particularly when the genes code for the gene products chitinase (ChiS, ChiG), glucanase (GluG), protein synthesis inhibitor (PSI) and antifungal protein (AFP).

2 Claims, 2 Drawing Sheets

SEQUENCE LISTING ( 1 ) GENERAL INFORMATION:

( i i i ) NUMBER OF SEQUENCES: 12

( 2 ) INFORMATION FOR SEQ ID NO: 1:

( i ) SEQUENCE CHARACTERISTICS:
        ( A ) LENGTH: 275 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: Aspergillus giganteus ( i x ) FEATURE:
        ( A ) NAME/KEY: 5'UTR
        ( B ) LOCATION: 1..45

( i x ) FEATURE:
        ( A ) NAME/KEY: CDS
        ( B ) LOCATION: 46..225
        ( C ) IDENTIFICATION METHOD: experimental
        ( D ) OTHER INFORMATION: /codon_start= 46
            / function= "antifungal agent"
            / product= "antifungal peptide"
            / evidence= EXPERIMENTAL
            / note= "antifungal agent, especially on
            Rhizoctonia solani, various Aspergillus, Fusaria
            and Trichophyton species"

( x i ) SEQUENCE DESCRIPTION: SEQ ID NO: 1:

```
TTGCCACCCC CGTTGAAGCC GATTCTCTCA CCGCTGGTGG TCTGG ATG CAA GAG                54
                                                    Met Gln Glu
                                                      1

ATG AGA GCG CGG GTT TTG GCC ACA TAC AAT GGC AAA TGC TAC AAG AAG            102
Met Arg Ala Arg Val Leu Ala Thr Tyr Asn Gly Lys Cys Tyr Lys Lys
      5                  10                  15

GAT AAT ATC TGC AAG TAC AAG GCA CAG AGC GGC AAG ACT GCC ATT TGC            150
Asp Asn Ile Cys Lys Tyr Lys Ala Gln Ser Gly Lys Thr Ala Ile Cys
 20              25                  30                      35

AAG TGC TAT GTC AAA AAG TGC CCC CGC GAC GGC GCG AAA TGC GAG TTT            198
Lys Cys Tyr Val Lys Lys Cys Pro Arg Asp Gly Ala Lys Cys Glu Phe
              40                  45                      50

GAC AGC TAC AAG GGG AAG TGC TAC TGC TAGACGGTGA GCGAAGGGAC                  245
Asp Ser Tyr Lys Gly Lys Cys Tyr Cys
              55                  60

GAAGTAGGCT GGGGGTTATT TTACTCTGCT                                           275
```

( 2 ) INFORMATION FOR SEQ ID NO: 2:

( i ) SEQUENCE CHARACTERISTICS:
        ( A ) LENGTH: 60 amino acids
        ( B ) TYPE: amino acid
        ( D ) TOPOLOGY: linear ( i i ) MOLECULE TYPE: protein ( x i ) SEQUENCE DESCRIPTION: SEQ ID NO: 2:

```
Met Gln Glu Met Arg Ala Arg Val Leu Ala Thr Tyr Asn Gly Lys Cys
 1               5                  10                  15

Tyr Lys Lys Asp Asn Ile Cys Lys Tyr Lys Ala Gln Ser Gly Lys Thr
              20                  25                  30
```

```
Ala  Ile  Cys  Lys  Cys  Tyr  Val  Lys  Lys  Cys  Pro  Arg  Asp  Gly  Ala  Lys
          35                      40                      45

Cys  Glu  Phe  Asp  Ser  Tyr  Lys  Gly  Lys  Cys  Tyr  Cys
     50                       55                      60
```

(2) INFORMATION FOR SEQ ID NO: 3:

(i) SEQUENCE CHARACTERISTICS:
      (A) LENGTH: 51 amino acids
      (B) TYPE: amino acid
      (D) TOPOLOGY: linear (ii) MOLECULE TYPE: protein (v) FRAGMENT TYPE: C-terminal (vi) ORIGINAL SOURCE:
      (A) ORGANISM: Aspergillus giganteus (ix) FEATURE:
      (A) NAME/KEY: Protein
      (B) LOCATION: 1..51
      (D) OTHER INFORMATION: /note= "active protein fragment of
         AFP"

(xi) SEQUENCE DESCRIPTION: SEQ ID NO: 3:

```
Ala  Thr  Tyr  Asn  Gly  Lys  Cys  Tyr  Lys  Lys  Asp  Asn  Ile  Cys  Lys  Tyr
1                    5                       10                      15

Lys  Ala  Gln  Ser  Gly  Lys  Thr  Ala  Ile  Cys  Lys  Cys  Tyr  Val  Lys  Lys
               20                      25                      30

Cys  Pro  Arg  Asp  Gly  Ala  Lys  Cys  Glu  Phe  Asp  Ser  Tyr  Lys  Gly  Lys
          35                      40                      45

Cys  Tyr  Cys
     50
```

(2) INFORMATION FOR SEQ ID NO: 4:

(i) SEQUENCE CHARACTERISTICS:
      (A) LENGTH: 1032 base pairs
      (B) TYPE: nucleic acid
      (C) STRANDEDNESS: single
      (D) TOPOLOGY: linear (ii) MOLECULE TYPE: cDNA (vi) ORIGINAL SOURCE:
      (A) ORGANISM: Hordeum vulgare
      (B) STRAIN: L.cv. Piggy (vii) IMMEDIATE SOURCE:
      (A) LIBRARY: cDNA gene bank in lambda-gt-11-phages (ix) FEATURE:
      (A) NAME/KEY: 5'UTR
      (B) LOCATION: 1..42

(ix) FEATURE:
      (A) NAME/KEY: CDS
      (B) LOCATION: 43..885
      (D) OTHER INFORMATION: /codon_start= 43
         / function= "antifungal activity"
         / product= "protein synthesis inhibitor (PSI)"
         / note= "antifungal activity, especially on spores
         of Trichoderma reesii and Fusarium sporotrichoides
         and on Rhizoctonia solani."

(ix) FEATURE:
      (A) NAME/KEY: 3'UTR
      (B) LOCATION: 886..1032
      (D) OTHER INFORMATION: /partial
         / note= "46 nucleotides at the 3'-end not shown."

(ix) FEATURE:

( A ) NAME/KEY: polyA_signal
            ( B ) LOCATION: 930..935
            ( D ) OTHER INFORMATION: /note= "potential polyadenylation
                  signal"

( i x ) FEATURE:
            ( A ) NAME/KEY: polyA_signal
            ( B ) LOCATION: 963..976
            ( D ) OTHER INFORMATION: /note= "potential polyadenylation
                  signal"

( i x ) FEATURE:
            ( A ) NAME/KEY: polyA_signal
            ( B ) LOCATION: 1002..1011
            ( D ) OTHER INFORMATION: /note= "potential polyadenylation
                  signal"

( i x ) FEATURE:
            ( A ) NAME/KEY: mat_peptide
            ( B ) LOCATION: 46..886

( x i ) SEQUENCE DESCRIPTION: SEQ ID NO: 4:

| | | | | | | |
|---|---|---|---|---|---|---|
| CTTAATAGCA CATCTTGTCC GTCTTAGCTT TGCATTACAT CC ATG GCG GCA AAG | | | | | | 54 |
| | | | | Met Ala Ala Lys | | |
| | | | | 1 | | |

| ATG | GCG | AAG | AAC | GTG | GAC | AAG | CCG | CTC | TTC | ACC | GCG | ACG | TTC | AAC | GTC | 102 |
|---|---|---|---|---|---|---|---|---|---|---|---|---|---|---|---|---|
| Met | Ala | Lys | Asn | Val | Asp | Lys | Pro | Leu | Phe | Thr | Ala | Thr | Phe | Asn | Val | |
| 5 | | | | 10 | | | | | 15 | | | | | | 20 | |

| CAG | GCC | AGC | TCC | GCC | GAC | TAC | GCC | ACC | TTC | ATC | GCC | GGC | ATC | CGC | AAC | 150 |
|---|---|---|---|---|---|---|---|---|---|---|---|---|---|---|---|---|
| Gln | Ala | Ser | Ser | Ala | Asp | Tyr | Ala | Thr | Phe | Ile | Ala | Gly | Ile | Arg | Asn | |
| | | | | 25 | | | | | 30 | | | | | 35 | | |

| AAG | CTC | CGC | AAC | CCG | GCG | CAC | TTC | TCC | CAC | AAC | CGC | CCC | GTG | CTG | CCG | 198 |
|---|---|---|---|---|---|---|---|---|---|---|---|---|---|---|---|---|
| Lys | Leu | Arg | Asn | Pro | Ala | His | Phe | Ser | His | Asn | Arg | Pro | Val | Leu | Pro | |
| | | | 40 | | | | | 45 | | | | | 50 | | | |

| CCG | GTC | GAG | CCC | AAC | GTC | CCG | CCG | AGC | AGG | TGG | TTC | CAC | GTC | GTG | CTC | 246 |
|---|---|---|---|---|---|---|---|---|---|---|---|---|---|---|---|---|
| Pro | Val | Glu | Pro | Asn | Val | Pro | Pro | Ser | Arg | Trp | Phe | His | Val | Val | Leu | |
| | | 55 | | | | | 60 | | | | | 65 | | | | |

| AAG | GCC | TCG | CCG | ACC | AGC | GCC | GGG | CTC | ACG | CTG | GCC | ATT | CGG | GCG | GAC | 294 |
|---|---|---|---|---|---|---|---|---|---|---|---|---|---|---|---|---|
| Lys | Ala | Ser | Pro | Thr | Ser | Ala | Gly | Leu | Thr | Leu | Ala | Ile | Arg | Ala | Asp | |
| | | 70 | | | | | 75 | | | | | 80 | | | | |

| AAC | ATC | TAC | CTG | GAG | GGC | TTC | AAG | AGC | AGC | GAC | GGC | ACC | TGG | TGG | GAG | 342 |
|---|---|---|---|---|---|---|---|---|---|---|---|---|---|---|---|---|
| Asn | Ile | Tyr | Leu | Glu | Gly | Phe | Lys | Ser | Ser | Asp | Gly | Thr | Trp | Trp | Glu | |
| 85 | | | | | 90 | | | | | 95 | | | | | 100 | |

| CTC | ACC | CCG | GGC | CTC | ATC | CCC | GGC | GGC | ACC | TAC | GTC | GGG | TTC | GGC | GGC | 390 |
|---|---|---|---|---|---|---|---|---|---|---|---|---|---|---|---|---|
| Leu | Thr | Pro | Gly | Leu | Ile | Pro | Gly | Gly | Thr | Tyr | Val | Gly | Phe | Gly | Gly | |
| | | | | 105 | | | | | 110 | | | | | 115 | | |

| ACC | TAC | CGC | GAC | CTC | CTC | GGC | GAC | ACC | GAC | AAG | CTG | ACC | AAC | GTC | GCT | 438 |
|---|---|---|---|---|---|---|---|---|---|---|---|---|---|---|---|---|
| Thr | Tyr | Arg | Asp | Leu | Leu | Gly | Asp | Thr | Asp | Lys | Leu | Thr | Asn | Val | Ala | |
| | | | 120 | | | | | 125 | | | | | 130 | | | |

| CTC | GGC | CGG | CAG | CAG | CTC | CCG | GAC | GCG | GTG | ACC | GCC | CTC | CAC | GGG | CGC | 486 |
|---|---|---|---|---|---|---|---|---|---|---|---|---|---|---|---|---|
| Leu | Gly | Arg | Gln | Gln | Leu | Pro | Asp | Ala | Val | Thr | Ala | Leu | His | Gly | Arg | |
| | | | 135 | | | | | 140 | | | | | 145 | | | |

| ACC | AAG | GCC | GAC | AAG | CCG | TCC | GGC | CCG | AAG | CAG | CAG | CAG | GCG | AGG | GAG | 534 |
|---|---|---|---|---|---|---|---|---|---|---|---|---|---|---|---|---|
| Thr | Lys | Ala | Asp | Lys | Pro | Ser | Gly | Pro | Lys | Gln | Gln | Gln | Ala | Arg | Glu | |
| | | 150 | | | | | 155 | | | | | 160 | | | | |

| GCG | GTG | ACG | ACG | CTG | CTC | CTC | ATG | GTG | AAC | GAG | GCC | ACG | CGG | TTC | CAG | 582 |
|---|---|---|---|---|---|---|---|---|---|---|---|---|---|---|---|---|
| Ala | Val | Thr | Thr | Leu | Leu | Leu | Met | Val | Asn | Glu | Ala | Thr | Arg | Phe | Gln | |
| 165 | | | | | 170 | | | | | 175 | | | | | 180 | |

| ACG | GTG | TCT | GGG | TTC | GTG | GCC | GGG | TTG | CTG | CAC | CCC | AAG | GCG | GTG | GAG | 630 |
|---|---|---|---|---|---|---|---|---|---|---|---|---|---|---|---|---|
| Thr | Val | Ser | Gly | Phe | Val | Ala | Gly | Leu | Leu | His | Pro | Lys | Ala | Val | Glu | |
| | | | | 185 | | | | | 190 | | | | | 195 | | |

| AAG | AAG | AGC | GGG | AAG | ATC | GGC | AAT | GAG | ATG | AAG | GCC | CAG | GTG | AAC | GGG | 678 |
|---|---|---|---|---|---|---|---|---|---|---|---|---|---|---|---|---|
| Lys | Lys | Ser | Gly | Lys | Ile | Gly | Asn | Glu | Met | Lys | Ala | Gln | Val | Asn | Gly | |
| | | | | 200 | | | | | 205 | | | | | 210 | | |

| | | | | | | | | | | | | | | | | |
|---|---|---|---|---|---|---|---|---|---|---|---|---|---|---|---|---|
| TGG | CAG | GAC | CTG | TCC | GCG | GCG | CTG | CTG | AAG | ACG | GAC | GTG | AAG | CCT | CCG | 726 |
| Trp | Gln | Asp | Leu | Ser | Ala | Ala | Leu | Leu | Lys | Thr | Asp | Val | Lys | Pro | Pro | |
| | 215 | | | | | 220 | | | | | 225 | | | | | |
| CCG | GGA | AAG | TCG | CCA | GCG | AAG | TTC | GCG | CCG | ATC | GAG | AAG | ATG | GGC | GTG | 774 |
| Pro | Gly | Lys | Ser | Pro | Ala | Lys | Phe | Ala | Pro | Ile | Glu | Lys | Met | Gly | Val | |
| | 230 | | | | | 235 | | | | | 240 | | | | | |
| AGG | ACG | GCT | GTA | CAG | GCC | GCC | AAC | ACG | CTG | GGG | ATC | CTG | CTG | TTC | GTG | 822 |
| Arg | Thr | Ala | Val | Gln | Ala | Ala | Asn | Thr | Leu | Gly | Ile | Leu | Leu | Phe | Val | |
| 245 | | | | | 250 | | | | | 255 | | | | | 260 | |
| GAG | GTG | CCG | GGT | GGG | TTG | ACG | GTG | GCC | AAG | GCG | CTG | GAG | CTG | TTC | CAT | 870 |
| Glu | Val | Pro | Gly | Gly | Leu | Thr | Val | Ala | Lys | Ala | Leu | Glu | Leu | Phe | His | |
| | | | | 265 | | | | | 270 | | | | | 275 | | |
| GCG | AGT | GGT | GGG | AAA | TAGGTAGTTT | TCCAGGTATA | CCTGCATGGG | TAGTGTAAAA | | | | | | | | 925 |
| Ala | Ser | Gly | Gly | Lys | | | | | | | | | | | | |
| | | | 280 | | | | | | | | | | | | | |

GTCGAATAAA CATGTCACAG AGTGACGGAC TGATATAAAT AAATAAATAA ACGTGTCACA 985

GAGTTACATA TAAACAAATA AATAAATAAT TAAAAATGTC CAGTTTA 1032

( 2 ) INFORMATION FOR SEQ ID NO: 5:

( i ) SEQUENCE CHARACTERISTICS:
        ( A ) LENGTH: 281 amino acids
        ( B ) TYPE: amino acid
        ( D ) TOPOLOGY: linear ( i i ) MOLECULE TYPE: protein ( x i ) SEQUENCE DESCRIPTION: SEQ ID NO: 5:

| | | | | | | | | | | | | | | |
|---|---|---|---|---|---|---|---|---|---|---|---|---|---|---|
| Met | Ala | Ala | Lys | Met | Ala | Lys | Asn | Val | Asp | Lys | Pro | Leu | Phe | Thr | Ala |
| 1 | | | | 5 | | | | | 10 | | | | | 15 | |
| Thr | Phe | Asn | Val | Gln | Ala | Ser | Ser | Ala | Asp | Tyr | Ala | Thr | Phe | Ile | Ala |
| | | | 20 | | | | | 25 | | | | | 30 | | |
| Gly | Ile | Arg | Asn | Lys | Leu | Arg | Asn | Pro | Ala | His | Phe | Ser | His | Asn | Arg |
| | | | 35 | | | | | 40 | | | | | 45 | | |
| Pro | Val | Leu | Pro | Pro | Val | Glu | Pro | Asn | Val | Pro | Pro | Ser | Arg | Trp | Phe |
| | 50 | | | | | 55 | | | | | 60 | | | | |
| His | Val | Val | Leu | Lys | Ala | Ser | Pro | Thr | Ser | Ala | Gly | Leu | Thr | Leu | Ala |
| 65 | | | | | 70 | | | | | 75 | | | | | 80 |
| Ile | Arg | Ala | Asp | Asn | Ile | Tyr | Leu | Glu | Gly | Phe | Lys | Ser | Ser | Asp | Gly |
| | | | | 85 | | | | | 90 | | | | | 95 | |
| Thr | Trp | Trp | Glu | Leu | Thr | Pro | Gly | Leu | Ile | Pro | Gly | Gly | Thr | Tyr | Val |
| | | | | 100 | | | | | 105 | | | | | 110 | |
| Gly | Phe | Gly | Gly | Thr | Tyr | Arg | Asp | Leu | Leu | Gly | Asp | Thr | Asp | Lys | Leu |
| | | | 115 | | | | | 120 | | | | | 125 | | |
| Thr | Asn | Val | Ala | Leu | Gly | Arg | Gln | Gln | Leu | Pro | Asp | Ala | Val | Thr | Ala |
| | | 130 | | | | | 135 | | | | | 140 | | | |
| Leu | His | Gly | Arg | Thr | Lys | Ala | Asp | Lys | Pro | Ser | Gly | Pro | Lys | Gln | Gln |
| 145 | | | | | 150 | | | | | 155 | | | | | 160 |
| Gln | Ala | Arg | Glu | Ala | Val | Thr | Thr | Leu | Leu | Leu | Met | Val | Asn | Glu | Ala |
| | | | | 165 | | | | | 170 | | | | | 175 | |
| Thr | Arg | Phe | Gln | Thr | Val | Ser | Gly | Phe | Val | Ala | Gly | Leu | Leu | His | Pro |
| | | | | 180 | | | | | 185 | | | | | 190 | |
| Lys | Ala | Val | Glu | Lys | Lys | Ser | Gly | Lys | Ile | Gly | Asn | Glu | Met | Lys | Ala |
| | | | 195 | | | | | 200 | | | | | 205 | | |
| Gln | Val | Asn | Gly | Trp | Gln | Asp | Leu | Ser | Ala | Ala | Leu | Leu | Lys | Thr | Asp |
| | | 210 | | | | | 215 | | | | | 220 | | | |
| Val | Lys | Pro | Pro | Pro | Gly | Lys | Ser | Pro | Ala | Lys | Phe | Ala | Pro | Ile | Glu |
| 225 | | | | | 230 | | | | | 235 | | | | | 240 |

| Lys | Met | Gly | Val | Arg | Thr | Ala | Val | Gln | Ala | Ala | Asn | Thr | Leu | Gly | Ile |
|---|---|---|---|---|---|---|---|---|---|---|---|---|---|---|---|
| | | | | 245 | | | | 250 | | | | | | 255 | |

| Leu | Leu | Phe | Val | Glu | Val | Pro | Gly | Gly | Leu | Thr | Val | Ala | Lys | Ala | Leu |
|---|---|---|---|---|---|---|---|---|---|---|---|---|---|---|---|
| | | | | 260 | | | | 265 | | | | | 270 | | |

| Glu | Leu | Phe | His | Ala | Ser | Gly | Gly | Lys |
|---|---|---|---|---|---|---|---|---|

(2) INFORMATION FOR SEQ ID NO: 6:

(i) SEQUENCE CHARACTERISTICS:
        (A) LENGTH: 480 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Hordeum vulgare
        (B) STRAIN: L.cv. Piggy (vii) IMMEDIATE SOURCE:
        (A) LIBRARY: cDNA gene bank in lambda-gt-11-phages
        (B) CLONE: incomplete psi cDNA clone (ix) FEATURE:
        (A) NAME/KEY: CDS
        (B) LOCATION: 1..351
        (D) OTHER INFORMATION: /partial
        / codon_start= 1
        / function= "protein synthesis inhibitor"
        / product= "protein synthesis inhibitor"
        / standard_name= "PSI"
        / note= "aminoterminally incomplete protein from an incomplete PSI cDNA clone"

(ix) FEATURE:
        (A) NAME/KEY: 3'UTR
        (B) LOCATION: 352..487

(ix) FEATURE:
        (A) NAME/KEY: polyA_signal
        (B) LOCATION: 404..409
        (D) OTHER INFORMATION: /note= "potential polyadenylation signal"

(ix) FEATURE:
        (A) NAME/KEY: polyA_signal
        (B) LOCATION: 437..442
        (D) OTHER INFORMATION: /note= "potential polyadenylation signal"

(ix) FEATURE:
        (A) NAME/KEY: polyA_signal
        (B) LOCATION: 445..450
        (D) OTHER INFORMATION: /note= "potential polyadenylation signal"

(xi) SEQUENCE DESCRIPTION: SEQ ID NO: 6:

| GCG | GTG | ACG | ACG | CTG | CTC | CTC | ATG | GTG | AAC | GAG | GCC | ACG | CGG | TTC | CAG | 48 |
|---|---|---|---|---|---|---|---|---|---|---|---|---|---|---|---|---|
| Ala | Val | Thr | Thr | Leu | Leu | Leu | Met | Val | Asn | Glu | Ala | Thr | Arg | Phe | Gln | |
| 1 | | | | 5 | | | | | 10 | | | | | 15 | | |

| ACG | GTG | TCG | GGG | TTC | GTG | GCC | GGG | CTG | CTG | CAC | CCC | AAG | GCG | GTG | GAG | 96 |
|---|---|---|---|---|---|---|---|---|---|---|---|---|---|---|---|---|
| Thr | Val | Ser | Gly | Phe | Val | Ala | Gly | Leu | Leu | His | Pro | Lys | Ala | Val | Glu | |
| | | | 20 | | | | | 25 | | | | | 30 | | | |

| AAG | AAG | AGC | GGG | AAG | ATC | GGC | AAT | GAG | ATG | AAG | GCC | CAG | GTG | AAC | GGG | 144 |
|---|---|---|---|---|---|---|---|---|---|---|---|---|---|---|---|---|
| Lys | Lys | Ser | Gly | Lys | Ile | Gly | Asn | Glu | Met | Lys | Ala | Gln | Val | Asn | Gly | |
| | | 35 | | | | | 40 | | | | | 45 | | | | |

| TGG | CAG | GAC | CTG | TCC | GCG | GCG | CTG | CTG | AAG | ACG | GAC | GTG | AAG | CCC | CCG | 192 |
|---|---|---|---|---|---|---|---|---|---|---|---|---|---|---|---|---|
| Trp | Gln | Asp | Leu | Ser | Ala | Ala | Leu | Leu | Lys | Thr | Asp | Val | Lys | Pro | Pro | |
| | | 50 | | | | | 55 | | | | | 60 | | | | |

| CCG | GGA | AAG | TCG | CCA | GCG | AAG | TTC | ACG | CCG | ATC | GAG | AAG | ATG | GGC | GTG | 240 |
| Pro | Gly | Lys | Ser | Pro | Ala | Lys | Phe | Thr | Pro | Ile | Glu | Lys | Met | Gly | Val | |
| 65 | | | | 70 | | | | | 75 | | | | | | 80 | |

| AGG | ACT | GCT | GAG | CAG | GCT | GCG | GCT | ACT | TTG | GGG | ATC | CTG | CTG | TTC | GTT | 288 |
| Arg | Thr | Ala | Glu | Gln | Ala | Ala | Ala | Thr | Leu | Gly | Ile | Leu | Leu | Phe | Val | |
| | | | | 85 | | | | | 90 | | | | | 95 | | |

| GAG | GTG | CCG | GGT | GGG | TTG | ACG | GTG | GCC | AAG | GCG | CTG | GAG | CTG | TTT | CAT | 336 |
| Glu | Val | Pro | Gly | Gly | Leu | Thr | Val | Ala | Lys | Ala | Leu | Glu | Leu | Phe | His | |
| | | | 100 | | | | | 105 | | | | | 110 | | | |

| GCG | AGT | GGT | GGG | AAA | TAGGTAGTTT | TGCAGGTATA | CCTGCATGGG | TAAATGTAAA | 391 |
| Ala | Ser | Gly | Gly | Lys | | | | | |
| | | | 115 | | | | | | |

AGTCGAATAA AAATGTCACA GAGTGACGGA CTGATATAAA TAAATTAATA AACATGTCAT    451

CATGAGTGAC AGACTGATAT AAATAAATA    480

(2) INFORMATION FOR SEQ ID NO: 7:

(i) SEQUENCE CHARACTERISTICS:
        (A) LENGTH: 117 amino acids
        (B) TYPE: amino acid
        (D) TOPOLOGY: linear (ii) MOLECULE TYPE: protein (xi) SEQUENCE DESCRIPTION: SEQ ID NO: 7:

| Ala | Val | Thr | Thr | Leu | Leu | Leu | Met | Val | Asn | Glu | Ala | Thr | Arg | Phe | Gln |
| 1 | | | | 5 | | | | | 10 | | | | | 15 | |

| Thr | Val | Ser | Gly | Phe | Val | Ala | Gly | Leu | Leu | His | Pro | Lys | Ala | Val | Glu |
| | | | 20 | | | | | 25 | | | | | 30 | | |

| Lys | Lys | Ser | Gly | Lys | Ile | Gly | Asn | Glu | Met | Lys | Ala | Gln | Val | Asn | Gly |
| | | 35 | | | | | 40 | | | | | 45 | | | |

| Trp | Gln | Asp | Leu | Ser | Ala | Ala | Leu | Leu | Lys | Thr | Asp | Val | Lys | Pro | Pro |
| | 50 | | | | | 55 | | | | | 60 | | | | |

| Pro | Gly | Lys | Ser | Pro | Ala | Lys | Phe | Thr | Pro | Ile | Glu | Lys | Met | Gly | Val |
| 65 | | | | 70 | | | | | 75 | | | | | | 80 |

| Arg | Thr | Ala | Glu | Gln | Ala | Ala | Ala | Thr | Leu | Gly | Ile | Leu | Leu | Phe | Val |
| | | | | 85 | | | | | 90 | | | | | 95 | |

| Glu | Val | Pro | Gly | Gly | Leu | Thr | Val | Ala | Lys | Ala | Leu | Glu | Leu | Phe | His |
| | | | 100 | | | | | 105 | | | | | 110 | | |

| Ala | Ser | Gly | Gly | Lys |
| | | | 115 | |

(2) INFORMATION FOR SEQ ID NO: 8:

(i) SEQUENCE CHARACTERISTICS:
        (A) LENGTH: 2329 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Serratia marcescens (vii) IMMEDIATE SOURCE:
        (A) LIBRARY: Cosmid bank from Serratia marcescens (ix) FEATURE:
        (A) NAME/KEY: misc_feature
        (B) LOCATION: 1..2329
        (C) IDENTIFICATION METHOD: experimental
        (D) OTHER INFORMATION: /function="exo-chitinase"
            / product= "ChiS protein"
            / evidence= EXPERIMENTAL / note= "sequence listing of the ChiS gene from a plasmid pLChiS from E.coli A 5187"

( x i ) SEQUENCE DESCRIPTION: SEQ ID NO: 8:

```
CAGGGCGTTG  TCAATAATGA  CAACACCCTG  GCTGAAGAGT  GTGGTGCAAT  ACTGATAAAT    60
ATTTATCTTT  CCTTAATAGA  AAATTCACTA  TCCTTATTTG  TCATGTTTTC  TTTTATTTAT   120
ATGAAAATAA  ATTCACGCTT  GCTGAATAAA  ACCCAGTTGA  TAGCGCTCTT  GTTTTGCGC    180
CTTTTTTATT  TATAGTACTG  AATGTACGCG  GTGGGAATGA  TTATTTCGCC  ACGTGGAAAG   240
ACGCTGTTGT  TATTTATTGA  TTTTAACCTT  CGCGGATTAT  TGCGGAATTT  TTTCGCTTCG   300
GCAATGCATC  GCGACGATTA  ACTCTTTTAT  GTTTATCCTC  TCGGAATAAA  GGAATCAGTT   360
ATGCGCAAAT  TAATAAACC   GCTGTTGGCG  CTGTTGATCG  GCAGCACGCT  GTGTTCCGCG   420
GCGCAGGCCG  CCGCGCCGGG  CAAGCCGACC  ATCGCCTGGG  GCAACACCAA  GTTCGCCATC   480
GTTGAAGTTG  ACCAGGCGGC  TACCGCTTAT  AATAATTTGG  TGAAGGTAAA  AAATGCCGCC   540
GATGTTTCCG  TCTCCTGGAA  TTTATGGAAT  GGCGACACCG  GCACGACGGC  AAAAGTTTTA   600
TTAAATGGCA  AGAGGCGTG   GAGTGGTCCT  TCAACCGGAT  CTTCCGGTAC  GGCGAATTTT   660
AAAGTGAATA  AAGGCGGCCG  TTATCAAATG  CAGGTGGCAC  TGTGCAATGC  CGACGGCTGC   720
ACCGCCAGTG  ACGCCACCGA  AATTGTGGTA  GCCGACACCG  ACGGCAGCCA  TTTGGCGCCG   780
TTGAAAGAGC  CGCTGCTGGA  AAAGAATAAA  CCGTATAAAC  AGAACTCCGG  CAAAGTGGTC   840
GGTTCTTATT  TCGTCGAGTG  GGGCGTTTAC  GGGCGCAATT  TCACCGTCGA  CAAGATCCCG   900
GCGCAAAACC  TGACCCACCT  GCTGTACGGC  TTTATCCCGA  TCTGCGGCGG  CAATGGCATC   960
AACGACAGCC  TGAAAGAGAT  TGAAGGCAGC  TTCCAGGCGT  TGCAGCGCTC  CTGCCAGGGC  1020
CGCGAGGACT  TCAAAGTCTC  GATCCACGAT  CCGTTCGCCC  CGCTGCAAAA  AGCGCAGAAG  1080
GGCGTGACCG  CCTGGGATGA  CCCCTACAAG  GGCAACTTCG  CCAGCTGAT   GGCGCTGAAG  1140
CAGGCGCATC  CTGACCTGAA  AATCCTGCCG  TCGATCGGCG  GCTGGACGCT  GTCCGACCCG  1200
TTCTTCTTCA  TGGGCGACAA  GGTGAAGCGC  GATCGCTTCG  TCGGTTCGGT  GAAAGAGTTC  1260
CTGCAGACCT  GGAAGTTCTT  CGACGGCGTG  GATATCGACT  GGGAGTTCCC  GGGCGGCAAA  1320
GGCGCCAACC  CTAACCTGGG  CAGCCCGCAA  GACGGGGAAA  CCTATGTGCT  GCTGATGAAG  1380
GAGCTGCGGG  CGATGCTGGA  TCAGCTGTCG  GTGGAAACCG  GCCGCAAGTA  TGAGCTGACC  1440
TCCGCCATCA  GCGCCGGTAA  GGACAAGATC  GACAAGGTGG  CTTACAACGT  TGCGCAGAAC  1500
TCGATGGATC  ACATCTTCCT  GATGAGCTAC  GACTTCTATG  GCGCCTTCGA  TCTGAAGAAC  1560
CTGGGGCATC  AGACCGCGCT  GAATGCGCCG  GCCTGGAAAC  CGGACACCGC  CTACACCACG  1620
GTGAACGGCG  TCAATGCGCT  GCTGGCGCAG  GGCGTCAAGC  CGGGCAAAAT  CGTCGTCGGC  1680
ACCGCCATGT  ATGGCCGCGG  CTGGACCGGG  GTGAACGGCT  ACCAGAACAA  TATTCCGTTC  1740
ACCGGCACCG  CCACCGGGCC  GGTTAAAGGC  ACCTGGGAGA  ACGGTATCGT  GGACTACCGC  1800
CAAATCGCCG  GCCAGTTCAT  GAGCGGCGAG  TGGCAGTATA  CCTACGACGC  CACGGCGGAA  1860
GCGCCTTACG  TGTTCAAACC  TTCCACCGGC  GATCTGATCA  CCTTCGACGA  TGCCCGCTCG  1920
GTGCAGGCTA  AAGGCAAGTA  CGTGTTGGAT  AAGCAGCTGG  GCGGCCTGTT  CTCCTGGGAG  1980
ATCGACGCGG  ATAACGGCGA  TATTCTCAAC  AGCATGAACG  CCAGCCTGGG  CAACAGCGCC  2040
GGCGTTCAAT  AATCGGTTGC  AGTGGTTGCC  GGGGATATC   CTTTCGCCCC  CGGCTTTTTC  2100
GCCGACGAAA  GTTTTTTTAC  GCCGCACAGA  TTGTGGCTCT  GCCCCGAGCA  AAACGCGCTC  2160
ATCGGACTCA  CCCTTTTGGG  TAATCCTTCA  GCATTTCCTC  CTGTCTTTAA  CGGCGATCAC  2220
AAAAATAACC  GTTCAGATAT  TCATCATTCA  GCAACAAAGT  TTTGGCGTTT  TTTAACGGAG  2280
```

```
TTAAAAACCA    GTAAGTTTGT    GAGGGTCAGA    CCAATGCGCT    AAAAATGGG                    2329
```

( 2 ) INFORMATION FOR SEQ ID NO: 9:

( i ) SEQUENCE CHARACTERISTICS:
        ( A ) LENGTH: 1002 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: Hordeum vulgare
        ( B ) STRAIN: L.

( i x ) FEATURE:
        ( A ) NAME/KEY: 5'UTR
        ( B ) LOCATION: 1..63

( i x ) FEATURE:
        ( A ) NAME/KEY: CDS
        ( B ) LOCATION: 64..861
        ( D ) OTHER INFORMATION: /codon_start= 64
            / function= "chitinase"
            / product= "26 kD preprotein of chitinase G (ChiG)"
            / note= "antifungal activity, especially on
            Trichoderma reesii and Fusarium sporotrichoides as
            well as Rhizoctonia solani and Botrytis cinerea."

( i x ) FEATURE:
        ( A ) NAME/KEY: 3'UTR
        ( B ) LOCATION: 862..1002
        ( D ) OTHER INFORMATION: /partial
            / note= "11 nucleotides at 3'end not shown"

( i x ) FEATURE:
        ( A ) NAME/KEY: polyA_signal
        ( B ) LOCATION: 905..910
        ( D ) OTHER INFORMATION: /note= "potential polyadenylation
            signal"

( i x ) FEATURE:
        ( A ) NAME/KEY: sig_peptide
        ( B ) LOCATION: 64..294
        ( D ) OTHER INFORMATION: /note= "probable signal peptide
            sequence"

( i x ) FEATURE:
        ( A ) NAME/KEY: sig_peptide
        ( B ) LOCATION: 298..312
        ( D ) OTHER INFORMATION: /note= "probable signal peptide
            sequence"

( i x ) FEATURE:
        ( A ) NAME/KEY: sig_peptide
        ( B ) LOCATION: 349..378
        ( D ) OTHER INFORMATION: /note= "probable signal peptide
            sequence"

( i x ) FEATURE:
        ( A ) NAME/KEY: sig_peptide
        ( B ) LOCATION: 466..588
        ( D ) OTHER INFORMATION: /note= "probable signal peptide
            sequence"

( i x ) FEATURE:
        ( A ) NAME/KEY: sig_peptide
        ( B ) LOCATION: 607..861
        ( D ) OTHER INFORMATION: /note= "probable signal peptide
            sequence"

( i x ) FEATURE:
        ( A ) NAME/KEY: mat_peptide
        ( B ) LOCATION: 133..861

( x i ) SEQUENCE DESCRIPTION: SEQ ID NO: 9:

```
CCTACGACAG TAGCGTAACG GTAAACACCG AGTACGGTAC TCTGTGCTTT GTTGGCTCGC        60

ACA ATG AGA TCG CTC GCG GTG GTG GTG GCC GTG GTA GCC ACG GTG GCC         108
    Met Arg Ser Leu Ala Val Val Val Ala Val Val Ala Thr Val Ala
    -23         -20             -15                 -10

ATG GCC ATC GGC ACG GCG CGC GGC AGC GTG TCC TCC ATC GTC TCG CGC         156
Met Ala Ile Gly Thr Ala Arg Gly Ser Val Ser Ser Ile Val Ser Arg
            -5                  1               5

GCA CAG TTT GAC CGC ATG CTT CTC CAC CGC AAC GAC GGC GCC TGC CAG         204
Ala Gln Phe Asp Arg Met Leu Leu His Arg Asn Asp Gly Ala Cys Gln
    10              15                  20

GCC AAG GGC TTC TAC ACC TAC GAC GCC TTC GTC GCC GCC GCA GCC GCC         252
Ala Lys Gly Phe Tyr Thr Tyr Asp Ala Phe Val Ala Ala Ala Ala Ala
25              30                  35                          40

TTC CCG GGC TTC GGC ACC ACC GGC AGC GCC GAC GCC CAG AAG CGC GAG         300
Phe Pro Gly Phe Gly Thr Thr Gly Ser Ala Asp Ala Gln Lys Arg Glu
                45                  50                  55

GTG GCC GCC TTC CTA GCA CAG ACC TCC CAC GAG ACC ACC GGC GGG TGG         348
Val Ala Ala Phe Leu Ala Gln Thr Ser His Glu Thr Thr Gly Gly Trp
            60                  65                  70

GCG ACT GCA CCG GAC GGG GCC TTC GCC TGG GGC TAC TGC TTC AAG CAG         396
Ala Thr Ala Pro Asp Gly Ala Phe Ala Trp Gly Tyr Cys Phe Lys Gln
        75                  80                  85

GAA CGT GGC GCC TCC TCC GAC TAC TGC ACC CCG AGC GCA CAA TGG CCG         444
Glu Arg Gly Ala Ser Ser Asp Tyr Cys Thr Pro Ser Ala Gln Trp Pro
    90                  95                  100

TGC GCC CCC GGG AAG CGC TAC TAC GGC CGC GGG CCA ATC CAG CTC TCC         492
Cys Ala Pro Gly Lys Arg Tyr Tyr Gly Arg Gly Pro Ile Gln Leu Ser
105                 110                 115                 120

CAC AAC TAC AAC TAT GGA CCT GCC GGC CGG GCC ATC GGG GTC GAT CTG         540
His Asn Tyr Asn Tyr Gly Pro Ala Gly Arg Ala Ile Gly Val Asp Leu
                125                 130                 135

CTG GCC AAC CCG GAC CTG GTG GCC ACG GAC GCC ACT GTG GGC TTT AAG         588
Leu Ala Asn Pro Asp Leu Val Ala Thr Asp Ala Thr Val Gly Phe Lys
            140                 145                 150

ACG GCC ATC TGG TTC TGG ATG ACG GCG CAG CCG CCC AAG CCA TCG AGC         636
Thr Ala Ile Trp Phe Trp Met Thr Ala Gln Pro Pro Lys Pro Ser Ser
        155                 160                 165

CAT GCT GTG ATC GCC GGC CAG TGG AGC CCG TCA GGG GCT GAC CGG GCC         684
His Ala Val Ile Ala Gly Gln Trp Ser Pro Ser Gly Ala Asp Arg Ala
    170                 175                 180

GCA GGC CGG GTG CCC GGG TTT GGT GTG ATC ACC AAC ATC ATC AAC GGC         732
Ala Gly Arg Val Pro Gly Phe Gly Val Ile Thr Asn Ile Ile Asn Gly
185                 190                 195                 200

GGG ATC GAG TGC GGT CAC GGG CAG GAC AGC CGC GTC GCC GAT CGA ATC         780
Gly Ile Glu Cys Gly His Gly Gln Asp Ser Arg Val Ala Asp Arg Ile
                205                 210                 215

GGG TTT TAC AAG CGC TAC TGT GAC ATC CTC GGC GTT GGC TAC GGC AAC         828
Gly Phe Tyr Lys Arg Tyr Cys Asp Ile Leu Gly Val Gly Tyr Gly Asn
            220                 225                 230

AAC CTC GAT TGC TAC AGC CAG AGA CCC TTC GCC TAATTAATTA GTCATGTATT       881
Asn Leu Asp Cys Tyr Ser Gln Arg Pro Phe Ala
        235                 240

AATCTTGGCC CTCCATAAAA TACAATAAGA GCATCGTCTC CTATCTACAT GCTGTAAGAT       941

GTAACTATGG TAACCTTTTA TGGGAACAT AACAAAGGCA TCTCGTATAG ATGCTTTGCT       1001

A                                                                      1002
```

( 2 ) INFORMATION FOR SEQ ID NO:10:

( i ) SEQUENCE CHARACTERISTICS:

(A) LENGTH: 266 amino acids
(B) TYPE: amino acid
(D) TOPOLOGY: linear (ii) MOLECULE TYPE: protein (xi) SEQUENCE DESCRIPTION: SEQ ID NO: 10:

| Met -23 | Arg | Ser | Leu | Ala -20 | Val | Val | Val | Ala -15 | Val | Val | Ala | Thr | Val -10 | Ala | Met |
|---|---|---|---|---|---|---|---|---|---|---|---|---|---|---|---|
| Ala | Ile | Gly -5 | Thr | Ala | Arg | Gly | Ser 1 | Val | Ser | Ser | Ile 5 | Val | Ser | Arg | Ala |
| Gln 10 | Phe | Asp | Arg | Met | Leu 15 | Leu | His | Arg | Asn | Asp 20 | Gly | Ala | Cys | Gln | Ala 25 |
| Lys | Gly | Phe | Tyr | Thr 30 | Tyr | Asp | Ala | Phe | Val 35 | Ala | Ala | Ala | Ala | Ala 40 | Phe |
| Pro | Gly | Phe | Gly 45 | Thr | Thr | Gly | Ser | Ala 50 | Asp | Ala | Gln | Lys | Arg 55 | Glu | Val |
| Ala | Ala | Phe 60 | Leu | Ala | Gln | Thr | Ser 65 | His | Glu | Thr | Thr | Gly 70 | Gly | Trp | Ala |
| Thr | Ala 75 | Pro | Asp | Gly | Ala | Phe 80 | Ala | Trp | Gly | Tyr | Cys 85 | Phe | Lys | Gln | Glu |
| Arg 90 | Gly | Ala | Ser | Ser | Asp 95 | Tyr | Cys | Thr | Pro | Ser 100 | Ala | Gln | Trp | Pro | Cys 105 |
| Ala | Pro | Gly | Lys | Arg 110 | Tyr | Tyr | Gly | Arg | Gly 115 | Pro | Ile | Gln | Leu | Ser 120 | His |
| Asn | Tyr | Asn | Tyr 125 | Gly | Pro | Ala | Gly | Arg 130 | Ala | Ile | Gly | Val | Asp 135 | Leu | Leu |
| Ala | Asn | Pro 140 | Asp | Leu | Val | Ala | Thr 145 | Asp | Ala | Thr | Val | Gly 150 | Phe | Lys | Thr |
| Ala | Ile 155 | Trp | Phe | Trp | Met | Thr 160 | Ala | Gln | Pro | Pro | Lys 165 | Pro | Ser | Ser | His |
| Ala 170 | Val | Ile | Ala | Gly | Gln 175 | Trp | Ser | Pro | Ser | Gly 180 | Ala | Asp | Arg | Ala | Ala 185 |
| Gly | Arg | Val | Pro | Gly 190 | Phe | Gly | Val | Ile | Thr 195 | Asn | Ile | Ile | Asn | Gly 200 | Gly |
| Ile | Glu | Cys | Gly 205 | His | Gly | Gln | Asp | Ser 210 | Arg | Val | Ala | Asp | Arg 215 | Ile | Gly |
| Phe | Tyr | Lys 220 | Arg | Tyr | Cys | Asp | Ile 225 | Leu | Gly | Val | Gly | Tyr 230 | Gly | Asn | Asn |
| Leu | Asp 235 | Cys | Tyr | Ser | Gln | Arg 240 | Pro | Phe | Ala | | | | | | |

(2) INFORMATION FOR SEQ ID NO:11:

(i) SEQUENCE CHARACTERISTICS:
(A) LENGTH: 1235 base pairs
(B) TYPE: nucleic acid
(C) STRANDEDNESS: single
(D) TOPOLOGY: linear (ii) MOLECULE TYPE: cDNA (vi) ORIGINAL SOURCE:
(A) ORGANISM: Hordeum vulgare
(B) STRAIN: L.

(ix) FEATURE:
(A) NAME/KEY: 5'UTR
(B) LOCATION: 1..48

(ix) FEATURE:
(A) NAME/KEY: CDS (B) LOCATION: 49..1050
(D) OTHER INFORMATION: /partial
  / codon_start= 49
  / function= "glucanase"
  / product= "preprotein of the glucanase GluG"

(ix) FEATURE:
  (A) NAME/KEY: 3'UTR
  (B) LOCATION: 1051..1235
  (D) OTHER INFORMATION: /partial
    / note= "14 nucleotides at the 3'end not shown."

(ix) FEATURE:
  (A) NAME/KEY: polyA_signal
  (B) LOCATION: 1083..1088
  (D) OTHER INFORMATION: /note= "potential polyadenylation signal"

(ix) FEATURE:
  (A) NAME/KEY: polyA_signal
  (B) LOCATION: 1210..1215
  (D) OTHER INFORMATION: /note= "potential polyadenylation signal"

(ix) FEATURE:
  (A) NAME/KEY: mat_peptide
  (B) LOCATION: 133..1050

(xi) SEQUENCE DESCRIPTION: SEQ ID NO: 11:

```
GGCAGCATTG CATAGCATTT GAGCACCAGA TACTCCGTGT GTGCACCA ATG GCT AGA         57
                                                      Met Ala Arg
                                                      -28

AAA GAT GTT GCC TCC ATG TTT GCA GTT GCT CTC TTC ATT GGA GCA TTC        105
Lys Asp Val Ala Ser Met Phe Ala Val Ala Leu Phe Ile Gly Ala Phe
-25             -20              -15                     -10

GCT GCT GTT CCT ACG AGT GTG CAG TCC ATC GGC GTA TGC TAC GGC GTG        153
Ala Ala Val Pro Thr Ser Val Gln Ser Ile Gly Val Cys Tyr Gly Val
            -5                    1              5

ATC GGC AAC AAC CTC CCC TCC CGG AGC GAC GTG GTG CAG CTC TAC AGG        201
Ile Gly Asn Asn Leu Pro Ser Arg Ser Asp Val Val Gln Leu Tyr Arg
        10              15                  20

TCC AAG GGC ATC AAC GGC ATG CGC ATC TAC TTC GCC GAC GGG CAG GCC        249
Ser Lys Gly Ile Asn Gly Met Arg Ile Tyr Phe Ala Asp Gly Gln Ala
    25              30                  35

CTC TCG GCC GTC CGC AAC TCC GGC ATC GGC CTC ATC CTC GAC ATC GGC        297
Leu Ser Ala Val Arg Asn Ser Gly Ile Gly Leu Ile Leu Asp Ile Gly
40              45                  50                      55

AAC GAC CAG CTC GCC AAC ATC GCC GCC AGC ACC TCC AAC GCG GCC TCC        345
Asn Asp Gln Leu Ala Asn Ile Ala Ala Ser Thr Ser Asn Ala Ala Ser
                60                  65                  70

TGG GTC CAG AAC AAC GTG CGG CCC TAC TAC CCT GCC GTG AAC ATC AAG        393
Trp Val Gln Asn Asn Val Arg Pro Tyr Tyr Pro Ala Val Asn Ile Lys
            75              80                  85

TAC ATC GCC GCC GGC AAC GAG GTG CAG GGC GGC GCC ACG CAG AGC ATC        441
Tyr Ile Ala Ala Gly Asn Glu Val Gln Gly Gly Ala Thr Gln Ser Ile
            90              95                 100

CTG CCG GCC ATG CGC AAC CTC AAC GCG GCC CTC TCC GCG GCG GGG CTC        489
Leu Pro Ala Met Arg Asn Leu Asn Ala Ala Leu Ser Ala Ala Gly Leu
    105             110                 115

GGC GCC ATC AAG GTG TCC ACC TCC ATC CGG TTC GAC GAG GTG GCC AAC        537
Gly Ala Ile Lys Val Ser Thr Ser Ile Arg Phe Asp Glu Val Ala Asn
120             125                 130                 135

TCC TTC CCG CCC TCC GCC GGC GTG TTC AAG AAC GCC TAC ATG ACG GAC        585
Ser Phe Pro Pro Ser Ala Gly Val Phe Lys Asn Ala Tyr Met Thr Asp
            140                 145                 150
```

```
GTG  GCC  CGG  CTC  CTG  GCG  AGC  ACC  GGC  GCG  CCG  CTG  CTC  GCC  AAC  GTC       633
Val  Ala  Arg  Leu  Leu  Ala  Ser  Thr  Gly  Ala  Pro  Leu  Leu  Ala  Asn  Val
               155                      160                      165

TAC  CCC  TAC  TTC  GCG  TAC  CGT  GAC  AAC  CCC  GGG  AGC  ATC  AGC  CTG  AAC       681
Tyr  Pro  Tyr  Phe  Ala  Tyr  Arg  Asp  Asn  Pro  Gly  Ser  Ile  Ser  Leu  Asn
          170                      175                      180

TAC  GCG  ACG  TTC  CAG  CCG  GGC  ACC  ACC  GTG  CGT  GAC  CAG  AAC  AAC  GGG       729
Tyr  Ala  Thr  Phe  Gln  Pro  Gly  Thr  Thr  Val  Arg  Asp  Gln  Asn  Asn  Gly
     185                      190                      195

CTG  ACC  TAC  ACG  TCC  CTG  TTC  GAC  GCG  ATG  GTG  GAC  GCC  GTG  TAC  GCG       777
Leu  Thr  Tyr  Thr  Ser  Leu  Phe  Asp  Ala  Met  Val  Asp  Ala  Val  Tyr  Ala
200                      205                      210                      215

GCG  CTG  GAG  AAG  GCC  GGC  GCG  CCG  GCG  GTG  AAG  GTG  GTG  GTG  TCG  GAG       825
Ala  Leu  Glu  Lys  Ala  Gly  Ala  Pro  Ala  Val  Lys  Val  Val  Val  Ser  Glu
                    220                      225                      230

AGC  GGG  TGG  CCG  TCG  GCG  GGC  GGG  TTT  GCG  GCG  TCG  GCC  GGC  AAT  GCG       873
Ser  Gly  Trp  Pro  Ser  Ala  Gly  Gly  Phe  Ala  Ala  Ser  Ala  Gly  Asn  Ala
               235                      240                      245

CGG  ACG  TAC  AAC  CAG  GGG  CTG  ATC  AAC  CAC  GTC  GGC  GGG  GGC  ACG  CCC       921
Arg  Thr  Tyr  Asn  Gln  Gly  Leu  Ile  Asn  His  Val  Gly  Gly  Gly  Thr  Pro
          250                      255                      260

AAG  AAG  CGG  GAG  GCG  CTG  GAG  ACG  TAC  ATC  TTC  GCC  ATG  TTC  AAC  GAG       969
Lys  Lys  Arg  Glu  Ala  Leu  Glu  Thr  Tyr  Ile  Phe  Ala  Met  Phe  Asn  Glu
     265                      270                      275

AAC  CAG  AAG  ACC  GGG  GAC  GCC  ACG  GAG  AGG  AGC  TTC  GGG  CTC  TTC  AAC      1017
Asn  Gln  Lys  Thr  Gly  Asp  Ala  Thr  Glu  Arg  Ser  Phe  Gly  Leu  Phe  Asn
280                      285                      290                      295

CCG  GAC  AAG  TCG  CCG  GCA  TAC  AAC  ATC  CAG  TTC  TAGTACGTGT  AGCTACCTAG       1070
Pro  Asp  Lys  Ser  Pro  Ala  Tyr  Asn  Ile  Gln  Phe
               300                      305

CTCACATACC  TAAATAAATA  AGCTGCACGT  ACGTACGTAA  TGCGGCATCC  AAGTGTAACG              1130

TAGACACGTA  CATTCATCCA  TGGAAGAGTG  CAACCAAGCA  TGCGTTAACT  TCCTGGTGAT              1190

GATACATCAT  CATGGTATGA  ATAAAGATA  TGGAAGATGT  TATGA                                1235
```

( 2 ) INFORMATION FOR SEQ ID NO: 12:

( i ) SEQUENCE CHARACTERISTICS:
        ( A ) LENGTH: 334 amino acids
        ( B ) TYPE: amino acid
        ( D ) TOPOLOGY: linear ( i i ) MOLECULE TYPE: protein ( x i ) SEQUENCE DESCRIPTION: SEQ ID NO: 12:

```
Met  Ala  Arg  Lys  Asp  Val  Ala  Ser  Met  Phe  Ala  Val  Ala  Leu  Phe  Ile
-28            -25                 -20                      -15

Gly  Ala  Phe  Ala  Ala  Val  Pro  Thr  Ser  Val  Gln  Ser  Ile  Gly  Val  Cys
          -10                       -5                       1

Tyr  Gly  Val  Ile  Gly  Asn  Asn  Leu  Pro  Ser  Arg  Ser  Asp  Val  Val  Gln
 5                       10                      15                      20

Leu  Tyr  Arg  Ser  Lys  Gly  Ile  Asn  Gly  Met  Arg  Ile  Tyr  Phe  Ala  Asp
               25                      30                      35

Gly  Gln  Ala  Leu  Ser  Ala  Val  Arg  Asn  Ser  Gly  Ile  Gly  Leu  Ile  Leu
               40                      45                      50

Asp  Ile  Gly  Asn  Asp  Gln  Leu  Ala  Asn  Ile  Ala  Ala  Ser  Thr  Ser  Asn
               55                      60                      65

Ala  Ala  Ser  Trp  Val  Gln  Asn  Asn  Val  Arg  Pro  Tyr  Tyr  Pro  Ala  Val
          70                       75                      80
```

-continued

| | | | | | | | | | | | | | | | |
|---|---|---|---|---|---|---|---|---|---|---|---|---|---|---|---|
| Asn | Ile | Lys | Tyr | Ile | Ala | Ala | Gly | Asn | Glu | Val | Gln | Gly | Gly | Ala | Thr |
| 85 | | | | | 90 | | | | | 95 | | | | | 100 |
| Gln | Ser | Ile | Leu | Pro | Ala | Met | Arg | Asn | Leu | Asn | Ala | Ala | Leu | Ser | Ala |
| | | | | 105 | | | | | 110 | | | | | 115 | |
| Ala | Gly | Leu | Gly | Ala | Ile | Lys | Val | Ser | Thr | Ser | Ile | Arg | Phe | Asp | Glu |
| | | | 120 | | | | | 125 | | | | | 130 | | |
| Val | Ala | Asn | Ser | Phe | Pro | Pro | Ser | Ala | Gly | Val | Phe | Lys | Asn | Ala | Tyr |
| | | 135 | | | | | 140 | | | | | 145 | | | |
| Met | Thr | Asp | Val | Ala | Arg | Leu | Leu | Ala | Ser | Thr | Gly | Ala | Pro | Leu | Leu |
| | 150 | | | | | 155 | | | | | 160 | | | | |
| Ala | Asn | Val | Tyr | Pro | Tyr | Phe | Ala | Tyr | Arg | Asp | Asn | Pro | Gly | Ser | Ile |
| 165 | | | | | 170 | | | | | 175 | | | | | 180 |
| Ser | Leu | Asn | Tyr | Ala | Thr | Phe | Gln | Pro | Gly | Thr | Thr | Val | Arg | Asp | Gln |
| | | | | 185 | | | | | 190 | | | | | 195 | |
| Asn | Asn | Gly | Leu | Thr | Tyr | Thr | Ser | Leu | Phe | Asp | Ala | Met | Val | Asp | Ala |
| | | | 200 | | | | | 205 | | | | | 210 | | |
| Val | Tyr | Ala | Ala | Leu | Glu | Lys | Ala | Gly | Ala | Pro | Ala | Val | Lys | Val | Val |
| | | 215 | | | | | 220 | | | | | 225 | | | |
| Val | Ser | Glu | Ser | Gly | Trp | Pro | Ser | Ala | Gly | Gly | Phe | Ala | Ala | Ser | Ala |
| | 230 | | | | | 235 | | | | | 240 | | | | |
| Gly | Asn | Ala | Arg | Thr | Tyr | Asn | Gln | Gly | Leu | Ile | Asn | His | Val | Gly | Gly |
| 245 | | | | | 250 | | | | | 255 | | | | | 260 |
| Gly | Thr | Pro | Lys | Lys | Arg | Glu | Ala | Leu | Glu | Thr | Tyr | Ile | Phe | Ala | Met |
| | | | | 265 | | | | | 270 | | | | | 275 | |
| Phe | Asn | Glu | Asn | Gln | Lys | Thr | Gly | Asp | Ala | Thr | Glu | Arg | Ser | Phe | Gly |
| | | | 280 | | | | | 285 | | | | | 290 | | |
| Leu | Phe | Asn | Pro | Asp | Lys | Ser | Pro | Ala | Tyr | Asn | Ile | Gln | Phe | | |
| | | 295 | | | | | 300 | | | | | 305 | | | |

TRANSGENIC PATHOGEN-RESISTANT ORGANISM

This is a divisional of application No. 08/457,797, filed on Jun. 1, 1995, now U.S. Pat. No. 5,689,045, which is a continuation of Ser. No. 08/134,416, filed on Oct. 8, 1993, now abandoned.

FIELD OF THE INVENTION

The invention relates to a pathogen-resistant organism and to a process for generating it.

BACKGROUND OF THE INVENTION

It is known in the state of the art that infestations of a plant by pathogens causes a series of different reactions. These include, for example, changes in the cell wall structure, the synthesis of phytoalexins which have antimicrobial activity, the accumulation of so-called PR proteins (pathogenesis-related), protease inhibitors and enzymes with hydrolytic functions (Hahlbrock and Grisebach in Ann. Rev. Plant. Physiol., 30 (1979), 105–130).

Many pathogens (fungi and insects) have chitin as a constituent of their cell wall. By contrast, plants possess no chitin. It has now been demonstrated in some cases that there is enhanced production of chitinases in plants after infestation by pathogens. Chitinases are among the enzymes with hydrolytic functions and they catalyze chitin breakdown. It has now been possible to show that plants acquire an increased resistance to pathogens by the production of chitinases.

It is furthermore known to use a gene from barley plants whose gene product codes for an inhibitor of fungal protein synthesis. The incorporation of a corresponding inhibitor gene in transgenic plants led to improved resistance to fungi.

Finally, it has also been disclosed that the use of a polypeptide from *Aspergillus giganteus* is able to protect, by virtue of its antifungal activity, plants from infestation by fungi.

However, given this state of the art there is a need to provide further transgenic pathogen-resistant organisms. Moreover, the organisms which are particularly desired are those whose resistance is increased overall by comparison with the known organisms or is extended with respect to the number of possible pathogens.

This problem is solved by a transgenic pathogen-resistant organism having the features of the present invention.

The invention is based on the surprising finding that the incorporation of at least two different genes with pathogen-inhibiting action into the genome of an organism assists the latter to resist pathogens to an extent going far beyond an additive effect of each of the genes on its own.

The dependent claims indicate further embodiments of the invention.

The genes can code for gene products which reduce the vitality of fungi. In particular, the genes can be of fungal, bacterial and plant, animal or viral origin. In particular, the gene products have properties which promote resistance to fungi. The gene products are chitinase (ChiS, ChiG), glucanase (GluG), protein synthesis inhibitor (PSI) and antifungal protein (AFP).

The transgenic pathogen-resistant organism can be a plant, and tobacco, potato, strawberry, corn, rape or tomato plants are preferred.

The invention also relates to DNA-transfer vectors with inserted DNA sequences as are indicated in detail in this description.

The invention furthermore relates to a process for the generation of pathogen-resistant organisms as are described herein, wherein at least 1 gene with pathogen-inhibiting action is transferred into the genome of an organism, and the pathogen-resistant organism is obtained (a) by crossing the organism with another, optionally transgenic, organism which contains at least one other gene with pathogen-inhibiting action, and subsequently selecting, and/or (b) by transformation of this other gene with pathogen-inhibiting action into the organism. The process can be used with DNA-transfer vectors with inserted DNA sequences corresponding to a gene with pathogen-inhibiting action as described herein.

Finally, the invention relates to a process for the generation of pathogen-resistant organisms, wherein vectors which comprise more than one gene with pathogen-inhibiting action are used for the transformation into the genome of an organism.

The invention also relates to a process for ensuring the resistance of organisms to pathogens, characterized in that the organism used is a transgenic pathogen-resistant organism according to the present invention or an organism whose genome contains at least one gene complying with the definitions used herein, and at least one substance which is not expressed by the organism but corresponds to any other one of the gene products complying with the definitions given in this application is applied to the organism.

It was possible to achieve the synergistic effects very particularly with transgenic pathogen-resistant organisms to which the gene sequences which coded for proteins of the attached sequence listings A to E, or corresponded to the latter, were transferred or transfected.

ChiS:

A DNA fragment which is 1.8 Kb in size, that codes for a chitinase called ChiS (SEQ ID NO: 8) was isolated from the soil bacterium *Serratia marcescens*. In vitro investigations with purified ChiS protein showed that it is able effectively to inhibit the growth of fungi, even in low concentrations. The reason for the inhibition is that the ChiS protein has a chitinase activity which is able to damage the tips of the fungal hyphae. In this way the fungus is unable to grow further and is inhibited.

PSI:

The PSI gene originates from barley and codes for a protein which inhibits protein synthesis by fungi. In vitro tests show that even low concentrations of PSI are sufficient to inhibit various fungi such as, for example, *Rhizoctonia solani*.

AFP:

It is possible for a polypeptide which has antifungal activity to be isolated from the fermentation broth of *Aspergillus giganteus* and to be sequenced. This polypeptide is suitable as antifungal agent, for example as spraying agent and as preservative for industrial products and human and animal foods. It can furthermore be combined with other substances which have pesticidal activity, fertilizers or growth regulators. Inhibitory activities against fungi were detectable inter alia against various Aspergillus, Fusaria, Phytophthora and Trichophyton species.

ChiG and GluG:

Two genes which code, respectively, for a chitinase (ChiG) and glucanase (GluG) can be isolated from certain types of barley. Purified ChiG protein or GluG protein inhibits various phytopathogenic fungi in vitro (inter alia

*Rhizoctonia solani*) (see R. Leah et al., Journal of Biological Chemistry, Vol. 266, No. 3 (1991), pages 1564–1573).

SUMMARY OF THE INVENTION

The inventors have now found, completely surprisingly, that an at least binary combination of expression of PSI, AFP, ChiS, ChiG or GluG leads to synergistic effects in respect of the acquired resistance to fungi in transgenic plants. In particular, the effects of the individual substances in the combination are markedly exceeded. These include resistance to the fungus *Rhizoctonia solani*, Sclerotinia infestation, Botrytis infestation, etc.

Combinations according to the invention are (DNA and/or polypeptides):

(binary combinations)

ChiS, GluG; ChiS, PSI; ChiS, ChiG; ChiS, AFP; GluG, PSI; GluG, ChiG; GluG, AFP; PSI; ChiG; PSI, AFP; (ternary combinations)

ChiS, GluG, PSI; ChiS, GluG, ChiG; ChiS, GluG, AFP; GluG, PSI, ChiG; GluG, PSI, AFP; PSI, ChiG, AFP; ChiG, AFP, GluG (quaternary combinations)

ChiS, GluG, PSI, AFP; ChiS, GluG, PSI, ChiG; (quinary combination)

ChiS, GluG, PSI, AFP, ChiG

The invention furthermore relates to the combined use of the proteins with pathogen-inhibiting action, preferably ChiS, PSI, AFP, ChiG and GluG, against pathogens. Combined use also means in this context that at least a first pathogen-inhibiting substance is expressed by the organism and at least a second substance which has pathogen-inhibiting action is applied to the organism from outside.

The agents according to the invention also include those which contain the abovementioned proteins in at least binary combination. The agents according to the invention can contain other active substances besides the proteins. The other active substances can be pesticides, fertilizers and/or growth regulators, and the agents according to the invention can be prepared in various formulations such as concentrates, emulsions, powders, formulations or carriers, mixtures with other active substances, etc. The ChiS/PSI and AFP/PSI combination is particularly preferred. These proteins can be used particularly effectively to inhibit the growth of *Rhizoctonia solani*, especially in tobacco crops.

DETAILED DESCRIPTION OF THE INVENTION

Figure 1:
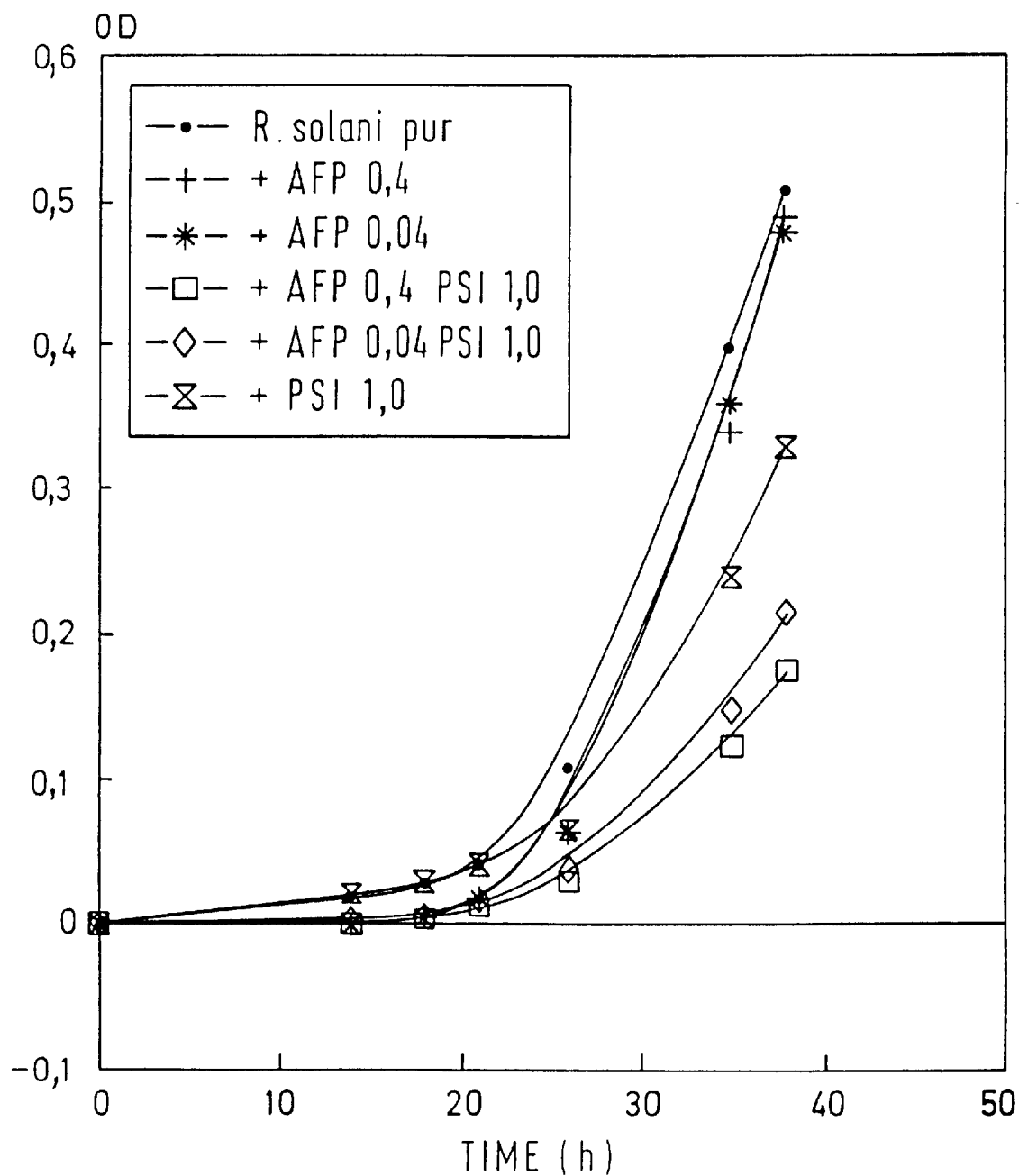
FIG. 1 shows the effects of AFP and PSI on *Rhizoctonia solani*.

The invention also relates to the use in a process according to the invention of a DNA sequence which codes at least for a polypeptide of sequences A to E, in which sequence A is the sequence of a 60 amino acid AFP protein (SEQ ID NO: 2); sequence A' is the sequence of 51 amino acid AFP protein (SEQ ID NO: 3); sequence B is the sequence of the PSI protein (SEQ ID NO: 5); sequence B' is the sequence of a protein encoded by an incomplete PSI-cDNA clone (SEQ ID NO: 7); sequence D is the sequence of the ChiG protein (SEQ ID NO: 10); and sequence E is the sequence of the GluG protein (SEQ ID NO: 12) or to a pathogen-resistant organism, where its genome contains at least two different genes under the control of active promoters with pathogen-inhibiting action, where the genes are in each case selected from the group of sequences A to E, in which sequence A is the sequence of a nucleic acid (SEQ ID NO: 1) which comprises a region encoding AFP protein; sequence B is the sequence of a nucleic acid (SEQ ID NO: 4) which comprises a region encoding PSI protein; sequence B' is the sequence of a nucleic acid (SEQ ID NO: 6) which was identified as a portion of an incomplete PSI-cDNA clone; sequence C is the sequence of a nucleic acid (SEQ ID NO: 8) encoding ChiS protein; sequence D is the sequence of a nucleic acid (SEQ ID NO: 9) which comprises a region encoding ChiG protein; and sequence E is the sequence of a nucleic acid (SEQ ID NO: 11) which comprises a region encoding GluG protein. The invention furthermore includes DNA sequences which hybridize with a DNA sequence which codes for polypeptides of amino-acid sequences A to E, in which sequence A is the sequence of a 60 amino acid AFP protein (SEQ ID NO: 2); sequence A' is the sequence of a 51 amino acid AFP protein (SEQ ID NO: 3); sequence B is the sequence of the PSI protein (SEQ ID NO: 5); sequence B' is the sequence of a protein encoded by an incomplete PSI-cDNA clone (SEQ ID NO: 7); sequence D is the sequence of the ChiG protein (SEQ ID NO: 10); and sequence E is the sequence of the GluG protein (SEQ ID NO: 12), where these DNA sequences can be of natural, synthetic or semisynthetic origin and can be related to the abovementioned DNA sequence by mutations, nucleotide substitutions, nucleotide deletions, nucleotide insertions and inversions of nucleotide sequences, and for a polypeptide with pathogenic activity. The invention furthermore relates to a recombinant DNA molecule which contains at least one DNA sequence which accords with the preceding statements, where this DNA molecule can be in the form of a cloning or expression vector.

The invention relates to appropriate host organisms and intermediate hosts which are transformed with a recombinant DNA molecule which accords with the preceding statements. Preferred as intermediate host in the generation of a pathogen-resistant transgenic organism are strains of bacteria, in particular so-called Agrobacteria strains.

The invention furthermore relates to the transgenic pathogen-resistant organisms obtained by the process according to the invention, in particular tobacco, potato, corn, pea, rape and tomato plants.

The DNA sequences according to the invention are, as a rule, transferred together with a promoter. Promoter sequences are recognized by the plant transcription apparatus and thus lead to constitutive expression of the gene associated with them in plants. The promoter can, however, also be pathogen-inducible and/or wound-inducible (WUN1) and/or tissue-specific and/or development-specific.

The genetic manipulation operations necessary for carrying out the invention, especially for expression of the gene in plants, are generally known. See for example the publication by Maniatis et al. in "Molecular cloning: A laboratory manual", Cold Spring Harbor (1982).

The invention is explained in detail in the following examples.

All the standard methods of molecular biology were carried out, unless otherwise indicated, as described by Maniatis et al. "Molecular cloning: a laboratory manual", Cold Spring Harbor (1982).

The DNA (SEQ ID NO: 1; SEQ ID NO: 4; SEQ ID NO: 6; SEQ ID NO: 8; SEQ ID NO: 9; SEQ ID NO: 11) coding for amino-acid sequences A to E (SEQ ID NO: 2; SEQ ID NO: 3; SEQ ID NO: 5; SEQ ID NO: 7; SEQ ID NO: 10; SEQ ID NO: 12) was initially cloned in a manner known per se and then transferred by conjugation into *A. Tumefaciens* LBA 4404 (A. Hoekema et al., Nature 303, 179–180). This took place by the method described by Van Haute et al. in EMBO J. 2, 411–418 (1983).

The transfer of DNA into that Agrobacterium was checked by isolating Agrobacterium DNA by the method described by Ebert et al. in Proc. Natl. Acad. Sci. USA 84 5745–5749 (1987). Restriction cleavage of the DNA, transfer to Hybond-N membrane (Amersham) and hybridization with a radioactively labeled DNA probe provided information about successful DNA transfer into the Agrobacterium.

The transformed Agrobacterium was then used to transform tobaco, rape, strawberry, tomato and potato plants.

The LBA4404 Agrobacteria required for the infection were initially cultivated in selective antibiotic medium (P. Zambrisky et al. in EMBO J., 1, 147–152 (1983)), sedimented by centrifugation and washed in YEB medium without antibiotics (YEB=0.5% meat extract; 0.2% yeast extract; 0.5% peptone; 0.5% sucrose; 2 mM $MgSO_4$). After renewed sedimentation and taking up in $MgSO_4$ it was possible to use the bacteria for the infection.

The so-called leaf disk method was used for the infection.

Sterile leaves were used for the leaf disk infection. Leaf pieces about 1 cm in size are dipped in the previously described Agrobacteria suspension and subsequently transferred to 3 MS medium (medium described by T. Murashige and F. Skoog in Physiol. Plant., 15, 473–497 (1962); 3MS= MS–3% sucrose). After incubation at 25° C. to 27° C. with 16 hours of light for two days, the leaf pieces were transferred to MSC16 medium (according to T. Murashige (see above); MSC16=MS+0.5 µg/ml BAP+0.1 µg/ml NAA+100 µg/ml kanamycin sulfate+500 µg/ml Claforan). Shoots appearing after 4–6 weeks were cut off and transplanted to MSC15 medium (according to Murashige (see above); MSC15=MS+2% sucrose, 500 µg/ml Claforan+100 µg/ml kanamycin sulfate). Shoots with root formation were analyzed further.

Monocotyledonous plants (including corn), but some dicotyledonous plants too, were transformed by direct gene transfer into protoplasts. These protoplasts were subsequently regenerated to intact plants (Example: J. Potrykus in Biotechnology 8 (1990), 535).

The resulting transgenic plants were infected with the fungus *Rhizoctonia solani* for testing purposes. For this purpose, fungal cultures were grown and thoroughly mixed in standard soil. This soil was then distributed in a dish and planted with the plants to be tested.

For the evaluation, each plant on a dish was assigned a value from 0 to 3. It was possible to calculate from this for each plant line an index which resulted from the sum of the values. The classification is as follows:

0=no symptoms (healthy)

1=slightly reduced size (compared with a non-infected control); no or very slight visible infestation 2=severe reduction in growth; severe symptoms of infestation 3=dead The rating is carried out in each case 14 days after the start of the series of tests.

EXAMPLE 1:

Fungus inhibition test with combined proteins

The intention initially was to show that the proteins used here have synergistic effects in their combination. Fungal growth tests in vitro were carried out for this purpose.

These entailed a defined amount of *Rhizoctonia solani* fungal mycelium being mixed with 100 µl of potato dextrose solution and incubated in microtiter plates at 25° C. In this test there is a linear correlation between the growth of the fungus and the increase in the optical density at 405 nanometers. The inhibitory effect of proteins can be detected from a smaller increase in the optical density.

2–3 mycelium balls were taken from a liquid culture of *R. solani*, mixed with 100 µl of KGB medium in an Eppendorf vessel and carefully homogenized with a glass mortar. This suspension was then mixed with 10 ml of KGB medium and passed through a sterile 100 µm screen. The optical density of this mycelium fragment suspension (100 µl aliquot) was adjusted to a value of 0.06–0.07 at 405 nanometers by adding medium. 100 µl samples were placed on a microtiter plate and mixed with the proteins to be tested. 7 parallels were measured per mixture. Mixtures which were mixed with the corresponding amounts of buffer served as controls. The plates were incubated in the dark at 25° C. for 48 hours, and the optical density of the cultures was measured at regular intervals.

Calculation of whether two proteins act together in an additive synergistic or antagonistic manner in the inhibition of fungal growth is possible from the measured data with the aid of the Colby formula which is described hereinafter and generally used (S. R. Colby in Wheeds, 15 (1967), 20–22).

To do this it was initially necessary to calculate the growth inhibition E to be expected theoretically with an additive behavior (the expected efficacy). This is given by:

$$E = W1 + W2 - ((W1 \times W2)/100)$$

where W1 and W2 indicate the efficacies of the individual proteins, which is defined as that percentage deviation of the growth plot (in the presence of the protein) from the untreated control. The efficacy for a protein (at a defined time in the growth plot) is given by:

$$W1 = (OD(K) - OD(P))/OD(K) \times 100 \text{ (percent)}$$

In this, OD(K) is the optical density of the untreated control and OD(P) is the optical density of the culture treated with the protein.

Thus, on combined use of two proteins, the following statements were possible: if the efficacy G measured in the experiment is identical to the expected value E, the behavior is additive. If, on the other hand, G is greater than E, the behavior is synergistic.

Using this test model, it emerged that the proteins ChiS, PSI, AFP, ChiG and GluG used in the Example surprisingly have synergistic inhibitory effects on various fungi, and these effects were achieved both by the combination of two types of protein and by multiple combination of the above-mentioned proteins.

For example, the following values were determined from the combination of ChiS and PSI protein and from the combination of AFP protein and PSI protein on the fungus *Rhizoctonia solani* (in each case two different ChiS and AFP concentrations with a constant RIP concentration):

ChiS+PSI:

The expected values were: E1=29.9% and E2=44.5%

The measured values were: G1=60.4% and G2=64.1%

The proteins ChiS and PSI therefore act together in a synergistic manner in the inhibition of the growth of *R. solani*.

FIG. 1 shows the results obtained with the combination of the proteins and with the individual substances. According to the Figure, various ChiS concentrations (0.5 µg/ml and 0.05 µg/ml) are combined with PSi protein (1.0 µg/ml).

AFP+PSI:

The expected values were: E1=39.9% and E2=41.9%

The measured values were: G1=57.7% and G2=65.4%

Figure 2:
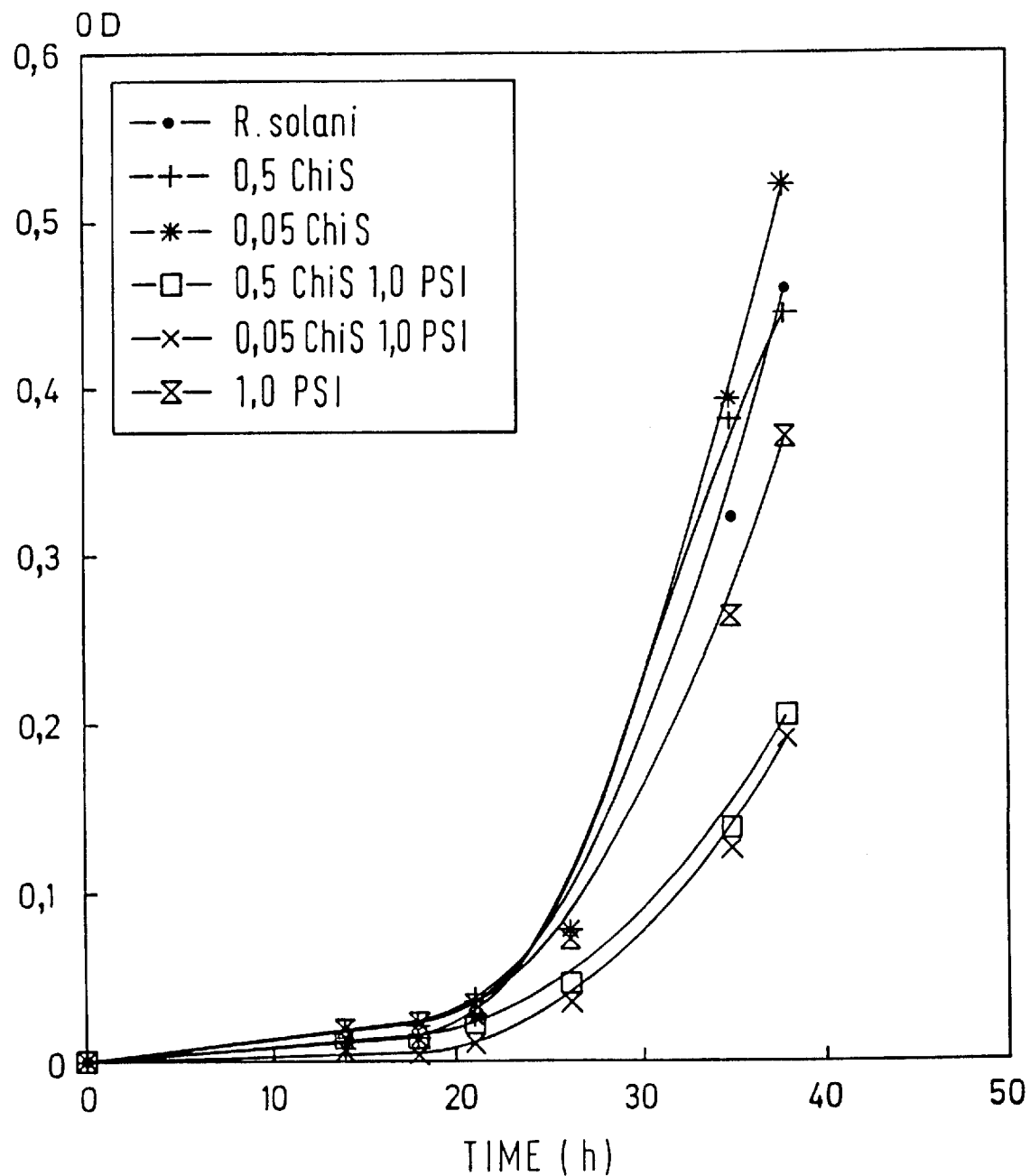
FIG. 2 shows the effects of ChiS and PSI on *Rhizoctonia solani*.

The AFP and PSI combination also according to this shows a synergistic inhibition of growth of the fungus *R. solani*. FIG. 2 indicates the test results with various AFP concentrations (0.4 µg/ml and 0.04 µg/ml) combined with PSI protein (1.0 µg/ml).

EXAMPLE 2:

Transgenic plants

In order to obtain the organisms according to the invention with DNA sequences which act together synergistically, initially transgenic plants which contained at least one of the genes which act together synergistically were generated.

ChiS in transgenic slants

Initially a ChiS gene was fused to plant regulatory sequences.

A ChiS gene 1.8 Kb in size was sequenced by using synthetic oligonucleotides in the dideoxy sequencing method of Sanger et al. in Proc. Natl. Acad. Sci. USA, 74 (1977), 5463–5467.

The 35S promoter originating from cauliflower mosaic virus (CamV) (400 bp (according to Töpfer et al. in Nucl. Acid. Res., 15 (1987), 5890)) underwent transcriptional fusion to the ChiS gene. The termination signal, which is 0.2 Kb in size, of the 35S gene of CamV, whose functionality in dicotyledonous plants is known, was used 3' from the ChiS gene. The chimeric gene 35S-ChiS was cloned into the pLS034 vector by means of the *Agrobacterium tumefaciens* transformation system in tobacco and potato plants, and kanamycin-resistant plants were regenerated.

It was possible to detect both the ChiS gene and the corresponding mRNA as well as the gene product protein in the resulting plants.

PSI in transgenic plants

PolyA RNA was initially isolated from ripe barley seeds (Hordeum vulgare L. cv. Piggy) and deposited in a cDNA gene bank λ-gt-11-phages. The details of the process are to be found in R. Lea in Plant. Biol., 12 (1989), 673–682. Monospecific PSI antibodies were then used to identify CDNA clones.

Subsequently, the PSI-positive λ-gt-11-phages were isolated, cloned further and sequenced by the dideoxy sequencing method of Sanger et al. indicated above. The DNA cloned into *E. coli* was then transferred in the manner described above by conjugation into Agrobacterium LBA4404.

Both the transferred gene and mRNA and gene product were detectable in corresponding transgenic tobacco, potato, rape, strawberry and tomato plants.

AFP in transgenic plants

For the cloning in the vector, the cDNA sequence of the antifungal peptide is provided with ends which can be ligated into BamH1 and Sal1 restriction cleavage sites. The cloning vector used was pDH51 (Pietrzak et al. in Nucl. Acids Res. 14 (1986), 5857). The vector pDH51 was opened with the restriction enzymes BamH1 and Sal1 between promoter and terminator. The vector pDH51 is a pUC18 derivative which contains promoter and terminator sequences of the 35S transcript from cauliflower mosaic virus. These sequences are recognized by the plant's transcription apparatus and lead to strong constitutive expression of the gene associated with them in plants. The DNA of the antifungal peptide is then cloned via the BamH1 and Sal1 cleavage site into the vector. Finally, the transcription unit—promoter, gene and terminator—is cut out of the vector using the restriction enzyme EcoRI and cloned into a plant transformation vector. The following vectors and their derivatives can, for example, be used as plant transformation vector:

pOCA18 (Olszewski et al. in Nucl. Acids Res., 16 (1988), 10765) pPCV310 (Koncz and Shell in MGG 204 (1986), 383) and pBin19 (Bevan et al. Nucl. Acids. Res. 12 (1984), 8711)

After the transcription unit and the vector had been ligated via the EcoRI cleavage site, the construct was conjugated into the Agrobacterium strain MP90RK (Koncz and Shell (see above)) or IHA101 (Hood et al. in J. Bacteriol. 168 (1986), 1291).

Transgenic tobacco, potato, strawberry, rape and tomato plants were then transformed by the method described above. Transformed shoots are selected on the basis of the cotransferred resistance to the antibiotic kanamycin. Expression of the antifungal protein in the transformed crop plants was checked and confirmed by DNA analysis (Southern blotting), RNA analysis (Northern blotting) and protein analysis with specific antibodies (Western blotting).

ChiG and GluG in transgenic plants

ChiG- and GluG-transgenic plants which were both Southern-, Northern- and Western-positive were obtainable in analogy to the plants described above.

ChiS, PSI, AFP, ChiG, GluG in transgenic monocotyledonous plants

It was possible by means of direct gene transfer to integrate the abovementioned genes into the genome of monocotyledonous plants such as, for example, corn. This resulted in transgenic plants which were Southern- and Northern- and Western-positive.

Combination of various fungus-resistance genes in transgenic plants

The previously obtained tobacco, corn, rape, strawberry, potato and tomato plants were crossed together and selected for plants containing in each case the fungus-resistant genes of both parents. In addition, transgenic plants were obtained by transforming them initially with one and then with one or more other gene. Finally, plants were also transformed with vectors which contained various resistance genes. Fungus-resistance tests were done with this plant material. Surprisingly, in all cases synergistic effects, not just additive effects, in respect of fungus resistance are observed.

For example, a tobacco plant which expresses ChiS and PSI shows a considerably greater resistance to Rhizoctonia infestation than the plants which expressed only ChiS or PSI or which would result from the additive resistance.

A synergistic inhibitory effect on infestation with *Rhizoctonia solani* also results from combined expression of PSI- and AFP-transgenic tobacco. Combination of two or more different genes (ChiS, RIP, AFP, ChiG and GluG) in a wide variety of transgenic plants also led to synergistic inhibitory effects on various fungi.

Whereas wild-type plants have index values from 38 to 46 in tests on 20 seedlings, it emerges with transgenic tobacco according to the invention that the latter grows as well in the presence of the fungus *Rhizoctonia solani* as do control plants (index value 10–12) cultivated on Rhizoctonia-free soil.

We claim:

1. A process for producing a plant having increased resistance to fungal attack, comprising topically applying, to a transgenic plant, a first gene product of a gene selected from the group consisting of a ChiG gene from barley, a GluG gene from barley, a PSI gene from barley, and an AFP gene from *Aspergillus giganteus,* wherein the transgenic plant carries at least two transgenes, each operably linked to a plant-functional promoter, wherein one transgene is a ChiS gene from *Serratia marcescens* and a second transgene is a gene selected from the group consisting of a ChiG gene from barley, a GluG gene from barley, a PSI gene from barley, and an AFP gene from *Aspergillus giganteus,* provided that the second transgene does not encode the first gene product.

2. A process for producing a plant having increased resistance to fungal attack, comprising topically applying, to a transgenic plant, a first gene product of a gene selected from the group consisting of a ChiG gene from barley, a GluG gene from barley, a PSI gene from barley, and a ChiS gene from *Serratia marcescens,* wherein the transgenic plant carries at least two transgenes, each operably linked to a plant-functional promoter, wherein one transgene is an AFP gene from *Aspergillus giganteus* and a second transgene is a gene selected from the group consisting of a ChiG gene from barley, a GluG gene from barley, a PSI gene from barley, and a ChiS gene from *Serratia marcescens,* provided that the second transgene does not encode the first gene product.

* * * * *